United States Patent
Davey et al.

[11] Patent Number: 6,120,483
[45] Date of Patent: *Sep. 19, 2000

[54] MEDICAL FLUID INFUSION AND ASPIRATION

[75] Inventors: Christopher T. Davey, Boston; Matthew N. McCarthy, Randolph, both of Mass.

[73] Assignee: Boston Scientific Corporation, Natick, Mass.

[*] Notice: This patent is subject to a terminal disclaimer.

[21] Appl. No.: 09/272,709

[22] Filed: Mar. 19, 1999

Related U.S. Application Data

[63] Continuation of application No. 08/943,046, Oct. 1, 1997, Pat. No. 5,928,203.

[51] Int. Cl.[7] .......................... A61M 25/00; F16L 11/00
[52] U.S. Cl. .......................... 604/247; 604/30; 604/236; 137/848
[58] Field of Search .......................... 604/30, 31, 33–35, 604/43–45, 118, 164, 246, 247, 264, 280–283, 236, 237, 537, 539; D24/110.6; 623/2; 137/849, 843, 846, 848

[56] References Cited

U.S. PATENT DOCUMENTS

| | | |
|---|---|---|
| 2,841,166 | 7/1958 | Auzin ........................................ 137/848 |
| 3,020,913 | 2/1962 | Heyer . |
| 3,111,125 | 11/1963 | Schulte . |
| 3,422,844 | 1/1969 | Grise . |
| 3,525,357 | 8/1970 | Koreski ..................................... 137/849 |
| 3,662,955 | 5/1972 | Takanaski ................................ 137/848 |
| 3,885,561 | 5/1975 | Cami . |
| 3,888,249 | 6/1975 | Spencer . |
| 4,134,402 | 1/1979 | Mahurkar ................................. 128/214 |
| 4,143,853 | 3/1979 | Abramson ................................ 251/149 |
| 4,327,722 | 5/1982 | Groshong et al. . |
| 4,342,315 | 8/1982 | Jackson . |
| 4,431,426 | 2/1984 | Groshong et al. ........................ 604/280 |
| 4,434,810 | 3/1984 | Atkinson .................................. 137/493 |
| 4,465,102 | 8/1984 | Rupp ........................................ 137/849 |

(List continued on next page.)

FOREIGN PATENT DOCUMENTS 0 476 796 A1   3/1992   European Pat. Off. .

*Primary Examiner*—Sharon Kennedy
*Attorney, Agent, or Firm*—Testa, Hurwitz & Thibeault LLP

[57] ABSTRACT

In an embodiment, a slit valve catheter has a generally tubular catheter body with an exterior surface exposed to an environment and an interior surface defining a lumen. The catheter further includes a valve which has a protuberance projecting radially from the catheter body.

14 Claims, 7 Drawing Sheets

U.S. PATENT DOCUMENTS

| | | |
|---|---|---|
| 4,475,898 | 10/1984 | Brodner et al. . |
| 4,529,399 | 7/1985 | Groshong et al. ............... 604/53 |
| 4,549,879 | 10/1985 | Groshong et al. . |
| 4,559,046 | 12/1985 | Groshong et al. . |
| 4,625,245 | 11/1986 | Weinstein . |
| 4,668,221 | 5/1987 | Luther ............... 604/164 |
| 4,671,796 | 6/1987 | Groshong et al. ............... 604/247 |
| 4,692,141 | 9/1987 | Mahurkar ............... 604/43 |
| 4,701,166 | 10/1987 | Groshong et al. ............... 604/247 |
| 4,737,152 | 4/1988 | Alchas . |
| 4,753,640 | 6/1988 | Nicols et al. . |
| 4,790,817 | 12/1988 | Luther ............... 604/53 |
| 4,798,594 | 1/1989 | Hillstead . |
| 4,813,934 | 3/1989 | Engelson et al. ............... 604/99 |
| 4,842,591 | 6/1989 | Luther ............... 604/283 |
| 4,950,252 | 8/1990 | Luther et al. ............... 604/198 |
| 4,973,319 | 11/1990 | Melsky . |
| 4,986,814 | 1/1991 | Burney et al. . |
| 4,994,046 | 2/1991 | Wesson et al. . |
| 4,995,863 | 2/1991 | Nichols et al. ............... 604/247 |
| 4,998,919 | 3/1991 | Schnepp-Pesch et al. . |
| 5,030,210 | 7/1991 | Alchas . |
| 5,085,635 | 2/1992 | Cragg . |
| 5,098,394 | 3/1992 | Luther ............... 604/167 |
| 5,112,301 | 5/1992 | Fenton, Jr. et al. . |
| 5,112,312 | 5/1992 | Luther ............... 604/177 |
| 5,120,317 | 6/1992 | Luther ............... 604/158 |
| 5,122,125 | 6/1992 | Duess ............... 604/282 |
| 5,147,332 | 9/1992 | Moorehead . |
| 5,149,327 | 9/1992 | Oshiyama . |
| 5,156,600 | 10/1992 | Young . |
| 5,160,325 | 11/1992 | Nichols et al. ............... 604/247 |
| 5,169,393 | 12/1992 | Moorehead et al. ............... 604/247 |
| 5,197,951 | 3/1993 | Mahurkar ............... 604/93 |
| 5,205,834 | 4/1993 | Moorehead et al. . |
| 5,207,655 | 5/1993 | Sheridan ............... 604/247 |
| 5,224,938 | 7/1993 | Fenton, Jr. . |
| 5,242,413 | 9/1993 | Heiliger . |
| 5,250,034 | 10/1993 | Appling et al. ............... 604/164 |
| 5,261,885 | 11/1993 | Lui . |
| 5,304,155 | 4/1994 | Lui . |
| 5,405,334 | 4/1995 | Roth et al. ............... 604/264 |
| 5,503,186 | 4/1996 | Orejola ............... 137/849 |
| 5,522,807 | 6/1996 | Luther . |
| 5,531,701 | 7/1996 | Luther ............... 604/165 |
| 5,533,988 | 7/1996 | Dickerson et al. ............... 604/282 |
| 5,554,136 | 9/1996 | Luther . |
| 5,556,390 | 9/1996 | Hicks ............... 604/280 |
| 5,569,217 | 10/1996 | Luther ............... 604/280 |
| 5,683,370 | 11/1997 | Luther et al. ............... 604/282 |
| 5,738,660 | 4/1998 | Luther ............... 604/164 |
| 5,743,882 | 4/1998 | Luther ............... 604/168 |
| 5,817,060 | 10/1998 | Overton et al. ............... 604/164 |
| 5,928,203 | 7/1999 | Davey et al. ............... 604/247 |

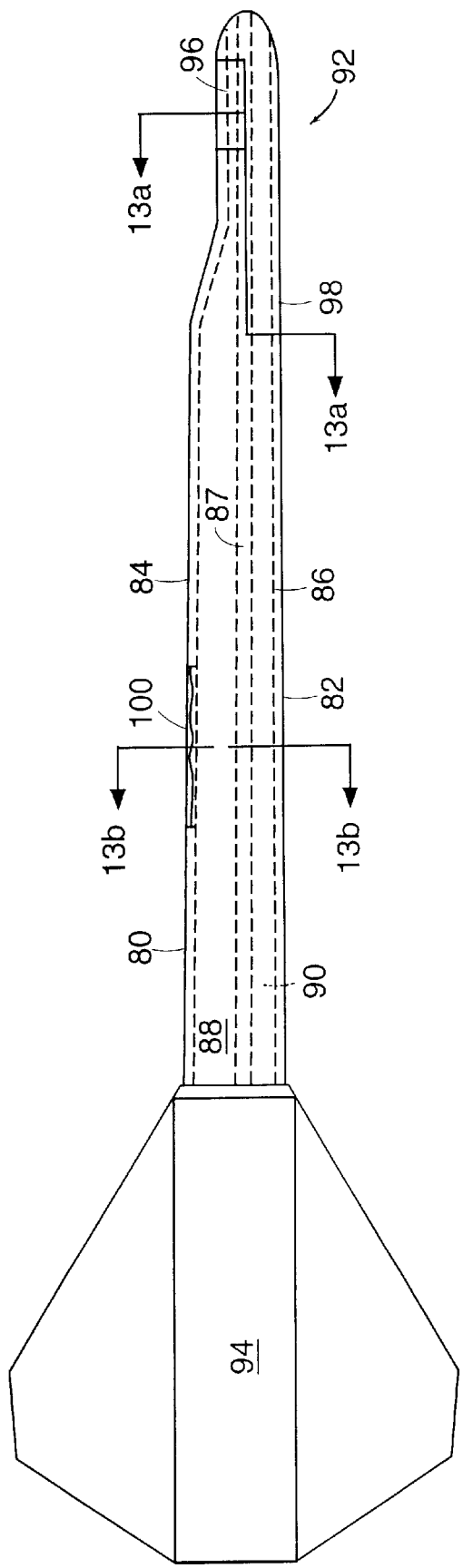
FIG. 12
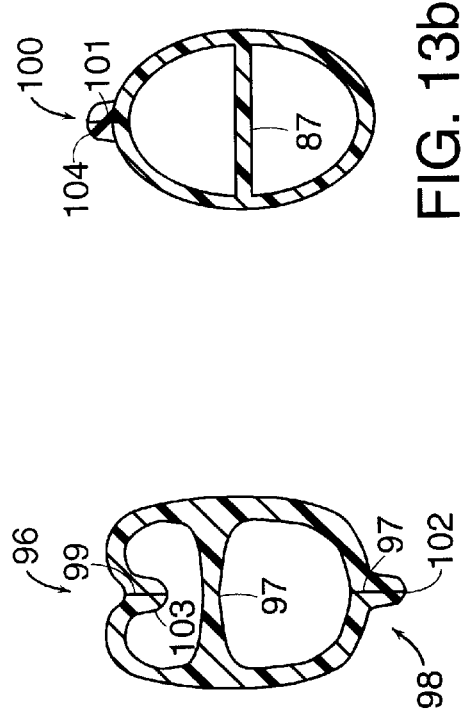
FIG. 13a
FIG. 13b

MEDICAL FLUID INFUSION AND ASPIRATION

CROSS-REFERENCE TO RELATED APPLICATION

This is a continuation of U.S. Ser. No. 08/943,046, field Oct. 1, 1997 now U.S. Pat. No. 5,928,203, issued Jul. 27, 1999.

FIELD OF THE INVENTION

This invention relates to medical fluid infusion and aspiration.

BACKGROUND OF THE INVENTION

Infusion of fluid into the body or aspiration of fluid from the body is often performed with a catheter which is inserted beneath the skin. The catheter has a lumen through which fluid can flow. In some designs, the lumen is closed at the insertion end of the catheter and fluid communication between the body environment outside the catheter and the lumen is controlled by a slit through the catheter wall which acts as a valve. The catheter has a hub on the end outside the body which can be connected to a syringe for increasing and decreasing the pressure inside the lumen.

For infusion, the fluid pressure inside the lumen is increased to force the catheter body adjacent the slit to flex outward, separating the opposing faces of the slit and forming an aperture through which fluid may pass to the body environment. For aspiration, the pressure inside the lumen is decreased to force the catheter body adjacent the slit to collapse inward, forming an aperture through which fluid may flow into the lumen. At neutral pressures, the catheter body assumes an unflexed condition in which the faces of the slit are opposed, which forms a seal to prevent infusion or aspiration.

A valve can be made to permit infusion only, aspiration only, or both infusion and aspiration. A valve that operates for infusion only can be formed by making the slit in a convex catheter wall portion, since the convex shape facilitates flexing outward while resisting flexing inward. A valve that operates for aspiration only can be formed by making the slit in a concave wall portion, which facilitates flexing inward while resisting flexing outward. A flat wall portion facilitates flexing in either direction and can be used to form a two-direction valve.

A two-direction valve may also be formed by chemical weakening of the catheter wall adjacent the slit, which facilitates flexing in both directions so that the valve works smoothly during infusion and aspiration. The lumen may also be shaped with a linear side that terminates to form regions of reduced catheter wall thickness. The regions act as hinges at which inward and outward flexing is enhanced and the area between the regions may have a greater wall thickness which facilitates sealing.

The catheter may also have multiple valves and multiple lumens. Further discussion of catheters is found, for example, in Groshong U.S. Pat. No. 4,549,879, Nichols U.S. Pat. No. 4,753,640, Lui U.S. Pat. No. 5,261,885, and Luther U.S. Pat. No. 5,522,807 the entire contents of all of which are incorporated herein by reference.

SUMMARY OF THE INVENTION

In one aspect, the invention features a slit valve catheter with an elongated, generally tubular catheter body having an exterior surface exposed to an environment and an interior surface defining a lumen. The catheter further includes a valve which has a protuberance projecting from the catheter body and a slit through the protuberance and catheter body.

In another aspect, the invention features a slit valve catheter having an elongated, generally tubular catheter body with an exterior surface exposed to an environment and an interior surface defining a lumen. The catheter further includes a valve with a generally convex exterior surface portion and a protuberance projecting radially outward from the convex exterior surface portion into the environment and a slit through the protuberance and catheter body. The interior surface defines a generally concave interior wall portion opposite the convex exterior surface portion.

In another aspect, the invention features a slit valve catheter with an elongated, generally tubular catheter body having an exterior surface exposed to an environment and an interior surface defining a lumen. The catheter further includes a valve with a generally concave exterior surface portion and a protuberance projecting radially inward from the interior surface opposite the concave exterior surface portion and a slit through the protuberance and catheter body and having a generally uniform wall thickness between the interior and exterior surface in portions adjacent the protuberance.

In another aspect, the invention features a slit valve catheter, having an elongated, generally tubular catheter body with an exterior surface exposed to an environment and an interior surface defining a lumen. The catheter further includes a first valve and a second valve. The first valve includes a protuberance projecting radially from the catheter body and a slit through the protuberance and catheter body.

In another aspect, the invention features a slit valve catheter with an elongated, generally tubular catheter body having an exterior surface exposed to an environment and an interior surface defining a first lumen and a second lumen. The catheter further includes a first valve to the first lumen which has a protuberance projecting radially from the catheter body and a slit through the protuberance and catheter body to the first lumen.

In another aspect, the invention features infusing fluid into a body or aspirating fluid from a body by delivering into the body a catheter having a generally elongated catheter body including an exterior surface exposed to the body and an interior surface defining a lumen. The catheter further includes an aspiration valve and an infusion valve, where at least one of the valves includes a protuberance projecting from the catheter body for permitting one of aspiration or infusion while resisting one of infusion or aspiration. The pressure in the lumen is varied to effect infusion or aspiration.

Embodiments may include one or more of the following features. The protuberance has a radial projection no greater than the outer diameter of the catheter body. The protuberance has a width no greater than twice a thickness of the catheter body measured between the exterior surface and the interior surface at a region adjacent the protuberance. The protuberance has a geometrical inflection near its point of maximum projection. (A geometrical inflection is the region where the curvature of the catheter (viewed in cross-section) changes from concave to convex or conversely, or the region in which the slope of a line tangent to the curvature is zero and the slope of lines adjacent the region have different signs.) The protuberance has a pair of inflections near the circumferential boundary of the protuberance. The protuberance is generally hemispherical. The protuberance is an integral extension of the catheter body. The protuberance extends axially no further than the valve. The protuberance extends axially substantially the length of the catheter body. The valve is on a sidewall of the catheter. The valve is on a forward-facing distal tip of the catheter.

Embodiments may also include one or more of the following. The valve includes a region having a convex exterior surface portion and the protuberance projects outwardly from the convex portion into the environment. The valve includes a region having a convex exterior surface portion and the protuberance projects inwardly from an interior surface portion opposite the convex surface portion. The valve includes a region having a concave exterior surface portion and the protuberance projects outwardly from the portion into the environment. The valve includes a region having a concave exterior surface portion and the protuberance projects inwardly from an interior surface portion opposite the concave exterior surface portion. The valve includes a region having a generally flat exterior surface portion and the protuberance projects outwardly from the flat exterior surface portion. The valve includes a region having a generally flat exterior surface portion and the protuberance projects inwardly from an interior surface portion opposite the flat exterior surface portion. The interior surface portion is generally flat. The catheter includes a first protuberance projecting from the exterior surface and a second protuberance projecting from the interior surface portion generally opposite the first protuberance. The radial projection of the first protuberance is different than the radial projection of the second protuberance.

Embodiments may also include one or more of the following. The interior surface is generally circular in cross-section. The exterior surface is generally circular in cross-section. The catheter has a generally uniform wall thickness between the interior and exterior surface in portions adjacent the protuberance.

Embodiments may also include one or more of the following. The catheter has a second valve and the second valve has a protuberance projecting radially from the catheter body and a slit through the protuberance and catheter body. The protuberance on the first valve projects from the exterior surface of the catheter into the environment and the protuberance on the second valve projects from the interior surface of the catheter body into the lumen. The first valve is proximal of the second valve. The second valve is on a forward-facing distal tip of the catheter. The slit catheter has a second valve to the first lumen. The catheter has a third valve to a second lumen.

Embodiments may also include one or more of the following. Both an aspiration and infusion valve are in communication with the same lumen and each include a protuberance. The protuberance on the aspiration valve being arranged to resist infusion and the protuberance on the infusion valve is arranged to resist aspiration. Alternately infusion and aspirating fluid from the body by increasing and delivering pressure in the lumen. The catheter may be delivered into the body over a guidewire.

Implementations may provide one or more advantages. For example, the protuberance may reduce leaks through the valve, especially leaks due to unintended valve openings when pressure conditions in the lumen are opposite to the intended valve operation direction. The protuberance can also control the level of lumen pressure needed to open the valve. The protuberance valves may be used on very thin-walled catheters in which the wall thickness is not sufficient to create an effective seal. A thinner catheter wall can provide a larger lumen, which may permit greater infusion and aspiration flow rates without substantially increasing the overall catheter diameter or the pressure differential needed to operate the valve.

Further aspects, features, and advantages follow.

DESCRIPTION OF THE PREFERRED EMBODIMENT(S)

We first briefly describe the drawings.
Drawings

FIG. 12 is a side view in partial cross-section of another embodiment;

FIG. 13a is an end-on cross-section along the line 13a—13a and FIG. 13b is an end-on cross-section along line 13b—13b in FIG. 12, with the valves in a condition where neither infusion, nor aspiration is taking place.

DESCRIPTION

Figure 1:
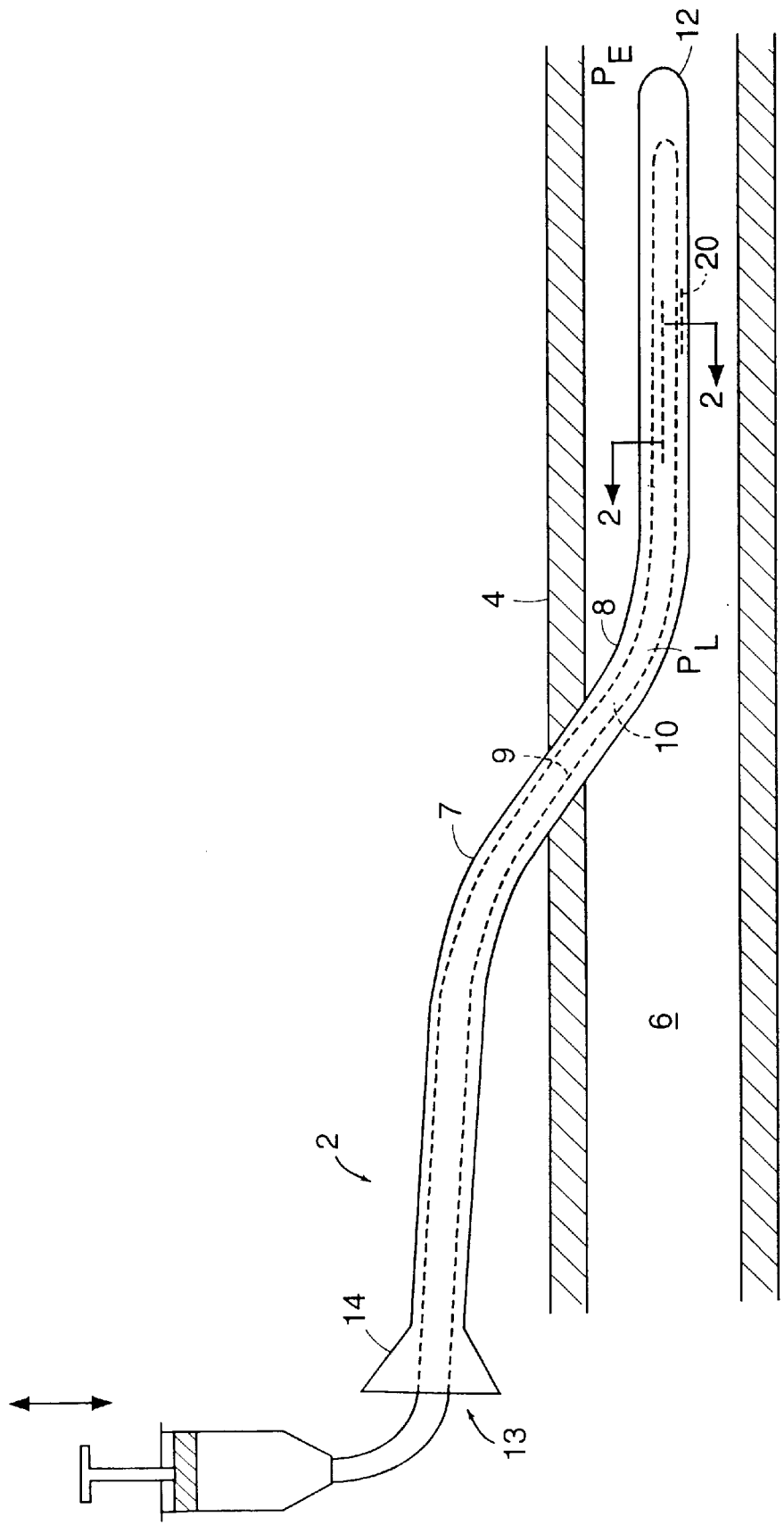
FIG. 1 is a side view, in partial cross-section, of a catheter in a vessel.

Referring to FIG. 1, a catheter 2 is placed beneath the skin 4 into, for example, a vessel 6 for either infusing fluid such as drug, nutrient, blood or other body fluid, into the body, or aspirating fluid from the body. The catheter includes an elongated polymeric member 7 which has an outer surface 8 exposed to the body environment and an inner surface 9 defining a lumen 10 which extends substantially the length of the catheter. The lumen is closed at the distal end 12 of the catheter and can be accessed at the proximal end 13 through a fitting 14, for example, a standard luer lock, which is connected to a syringe 16 or another suitable device for injecting or withdrawing fluid from the lumen 10.

The insertion portion of the catheter has a pair of slit valve regions, including a first valve region 18 and a second valve region 20, which permit fluid communication between the body environment and the lumen 10 by varying the pressure in the lumen, $P_L$, relative to the pressure in the body environment, $P_E$.

Figure 2:
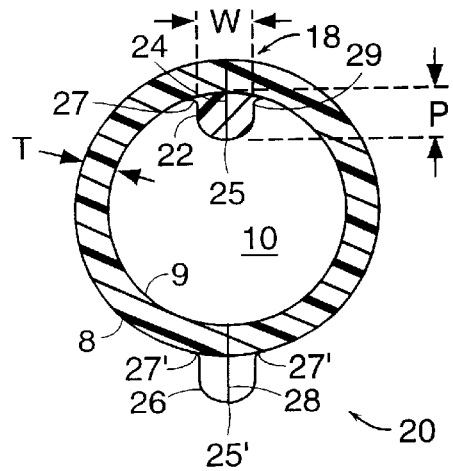
FIG. 2 is an end-on cross-section of a pair of valves as they would appear when viewed along the line 2—2 in FIG. 1, with the valves in a condition where neither infusion, nor aspiration is taking place.
Figure 3:
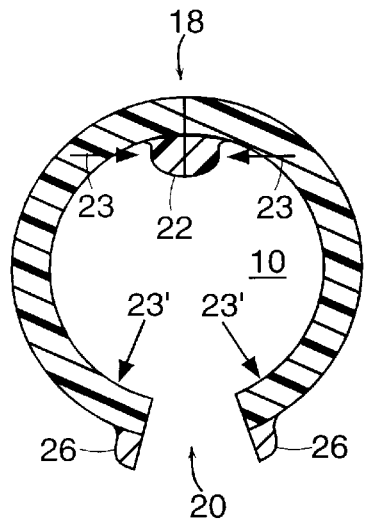
FIG. 3 is a similar end-on cross-section of the valves in FIG. 2 during infusion.
Figure 4:
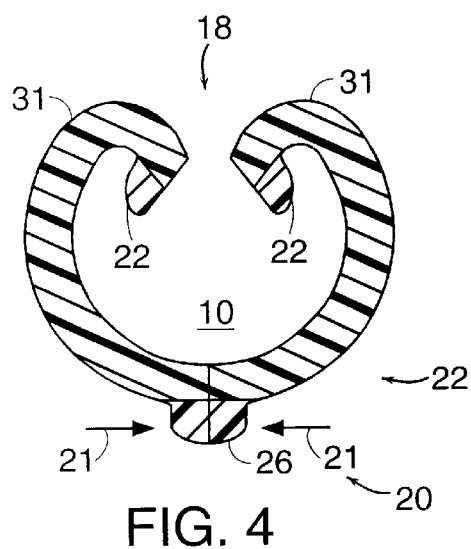
FIG. 4 is a similar end-on cross-section of the valves in FIG. 2, during aspiration.

Referring to FIGS. 2–4, one embodiment of a pair of valves, which are located in the valve regions 18, 20, is illustrated in a series of end-on cross-sectional views. In this case, the catheter cross-section is circular. In FIG. 2, the valve regions are shown in the condition in which the valves are sealed, for example, when the lumen pressure $P_L$ is essentially equal to the environmental pressure $P_E$. The first valve region 18 is used only for aspiration. The second valve region 20 is used only for infusion. Valve region 18 includes a slit 24 and valve region 26 includes a slit 28. The catheter has protuberances 22 having a width, W, between boundary inflection points and having a radial projection P from the catheter wall, which has a thickness T.

The valves also include protuberances 22, 26 which project from the catheter body. In this case, both valves have the same generally convex outer catheter walls, with the protuberances arranged to make the valves function as one-way valves in opposite directions; one one-way valve is for aspiration only and the other is for infusion only. The first valve region 18 has a generally convex outer wall surface with a protuberance 22 projecting from the inner wall surface into the lumen 10 of the catheter. Slit 24 extends through protuberance 22. The second valve region also has a generally convex outer wall surface but with a protuberance 26 projecting outward. Slit 28 also extends through protuberance 26.

Referring to FIG. 3, for infusion, the pressure in the lumen is increased, for example, by depressing the plunger 17 of the syringe 16 (FIG. 1), which creates the condition that the lumen pressure $P_L$ is greater than the environment pressure $P_E$. The increased lumen pressure acts upon the inwardly projecting protuberance 22 to create a greater sealing force (arrows 23) than in the absence of the protuberance. The secure seal prevents any uncontrolled infusion through the first valve region. In the second valve region 20, the increased lumen pressure creates a force (arrows 23') that causes the catheter wall to flex outwardly along a flexure region spaced from the slit; the protuberance 26 does not substantially inhibit opening of the slit valve, permitting a controlled infusion to take place.

Referring to FIG. 4, for aspiration, the pressure within the lumen is reduced by, for example, withdrawing the plunger 17 of the syringe 16 (FIG. 1). In the first valve region 18, the reduced pressure causes the catheter wall to flex inwardly along flexure regions 31; the protuberance 22 does not substantially interfere with the inward flexing of the valve, permitting controlled aspiration of fluid through the first valve. In the second valve region 20 the protuberance 26 resists inversion or collapse, under an external force 21 preventing uncontrolled aspiration through the second valve.

Figure 5:
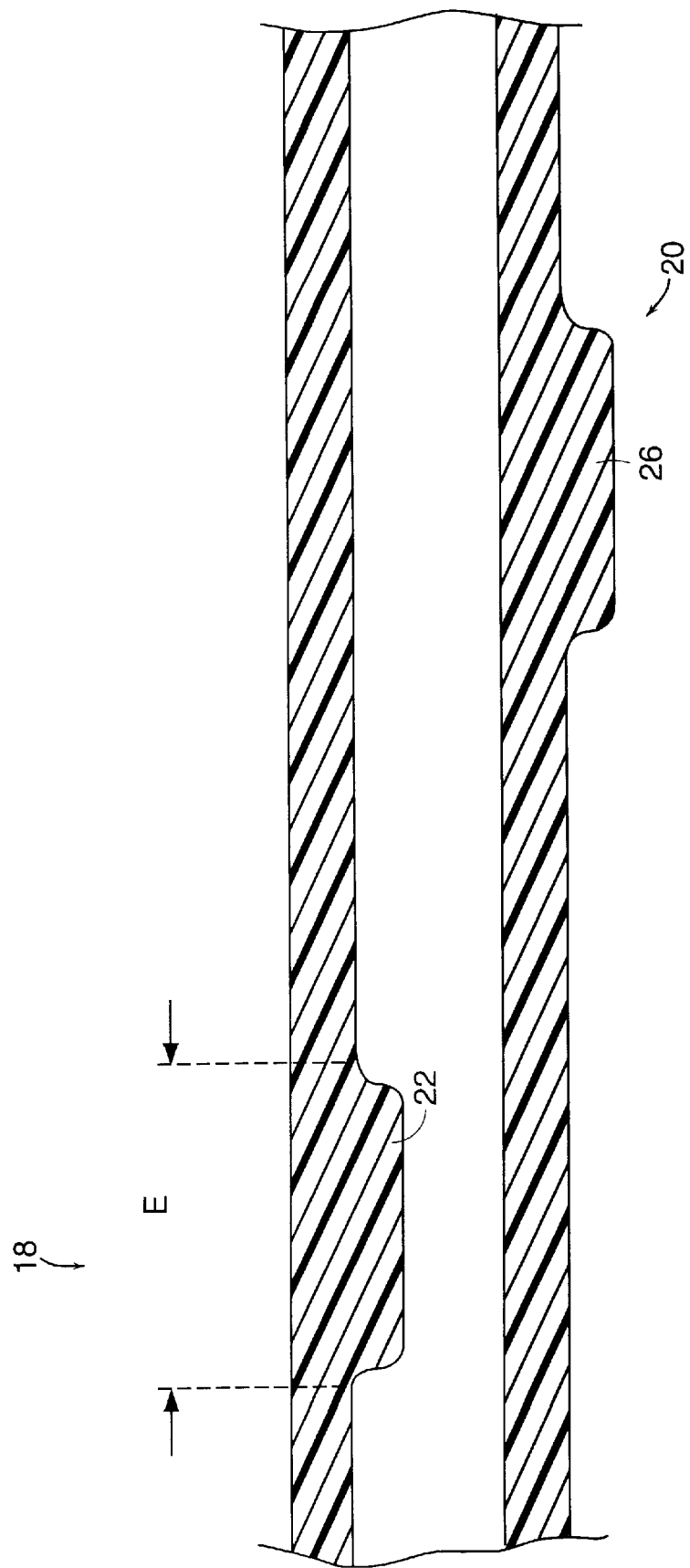
FIG. 5 is a longitudinal cross-section in the valve regions in FIG. 1.

The protuberances assist valve operation by projecting into the environment or lumen. For example, projection of the protuberance into a lumen increases sealing forces on the slit when the pressure in the lumen is increased because the protuberance modifies the contour about the slit such that the components of pressure vectors perpendicular to the slit are larger. The protuberances illustrated in the embodiment above are generally hemispherical with geometrical inflections 25, 25' at the location of greatest projection and further geometrical inflections 27, 27' and 29, 29' near or at the boundaries of the protuberance, where projection from the catheter body begins. Referring to FIG. 5, these protuberances also have short axial projections, which extend only within the valve regions and generally correspond to the length of the slit.

The shape and dimensions of the protuberance may be modified. The width of the protuberance is preferably about twice the thickness of the catheter body adjacent the protuberance or less. The projection of a protuberance into a lumen is preferably equal to or less than the lumen diameter. The protuberance may project across substantially the entire width of a lumen. The projection as measured from the outer surface of a catheter is preferably equal to or less than the outer diameter of the catheter. The protuberance may project from a catheter body having an otherwise uniform geometrical configuration, as indicated above, or the protuberance may project from a catheter body having an irregular or contoured inner and/or outer wall surface. The inflection points on either side of the protuberance are preferably spaced from the flexure or hinge region of the valve. The protuberance may also be asymmetrical in cross-section and may not have inflections at its boundaries, but instead extend smoothly from the otherwise uniform thickness and profile of the catheter wall. The protuberance may be oblong in shape.

One advantage is that the catheter may be operated at higher lumen pressures during infusion without inversion of the first valve which could lead to leaks or uncontrolled infusion. Similarly, the outwardly extending protuberance in the second valve region enhances sealing during aspiration through the first valve. Higher vacuum can be used during aspiration without inversion of the second valve. Alternatively, the catheter can be arranged for operation at lower pressure differentials for both infusion and aspiration. For example, the entire catheter body can be made of somewhat weak, thin-walled construction. The protuberance in the second valve region prevents collapse of the second valve during aspiration. During infusion through the second valve, the protuberance of the first valve prevents outward inversion. A protuberance can be used to make a one-way valve from a valve that would ordinarily operate for both infusion and aspiration. For example, the valve wall may be weakened by chemical treatment or by reducing the thickness of the polymer, which would ordinarily encourage valve action in either direction. However, a protuberance may be used to prevent valve action in one direction.

Manufacture

The catheters may be manufactured by injection molding or by modifying an extruded tube. For example, extrusion may be used to provide a uniform polymeric tube, to which a hub is attached at one end and the other end is sealed. Insert molding can then be used to provide the desired geometry of the slit regions. The slits could then be created in the desired valve locations as a subsequent mechanical operation. Insert molding allows the tip to be formed of a material either identical to or dissimilar from the catheter tube. The molded details in the protuberances include axial cross sectional geometry, protuberance longitudinal cross sectional geometry, protuberance length, wall thickness, degree of concave/convex curvature, etc. Other manufacturing techniques include melting or otherwise adhering the catheter portions as components or post-forming an extruded tube.

In particular embodiments, the polymer may be polyurethane, silicones, polyethylenes, nylons, polyesters and polyester elastomers. In one example, the catheter is polyurethane (e.g., Tecoflex, available from Thermedics, Woburn, Mass.). The overall OD of the catheter is about 3–16 French. The overall length of the catheter is about 20–60 cm. For example, a 5 French catheter may have a substantially constant catheter body wall thickness, T, (FIG. 2) of about 0.015 inch and lumen diameter of about 0.035 inch. Protuberances are hemispherical, have a radial projection, P, (FIG. 2) of about 0.015 inch, a longitudinal extension, E, (FIG. 5) of about 0.200 inch and a width, W, between boundary inflection points (FIG. 2) of about 0.030 inch. The slit is formed by a cutting device, such as a razor and has a length of 0.200 inch, substantially the same as the longitudinal projection of the protuberance.

Additional Embodiments

Figure 6:
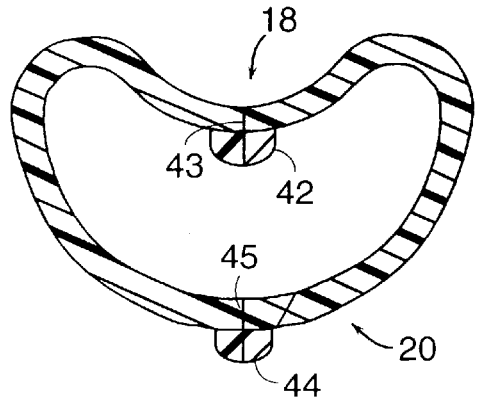
FIG. 6 is an end-on cross-section of another embodiment with a pair of valves as they would appear when viewed along the line 2—2 in FIG. 1, with the valves in a condition where neither infusion nor aspiration is taking place.
Figure 7:
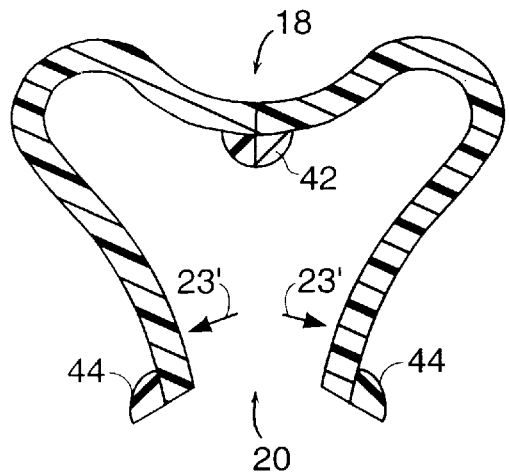
FIG. 7 is a similar end-on cross-section of the embodiment in FIG. 6, during infusion.
Figure 8:
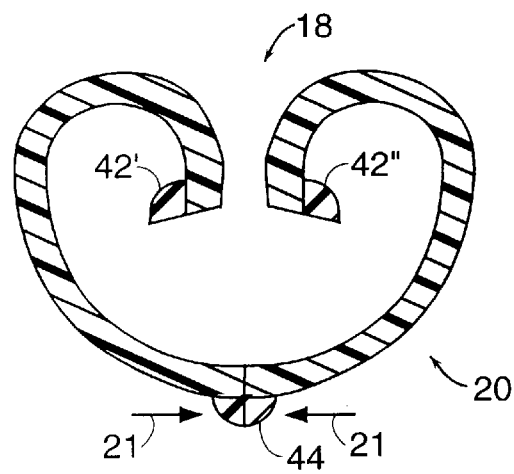
FIG. 8 is a similar end-on cross-section of the embodiment of FIG. 6 during aspiration.

Referring to FIGS. 6–8, another embodiment of a two-valve catheter is illustrated. In this case, the first valve region 18 is used for aspiration. It includes an outer wall surface that is generally concave and a slit in the wall of the concave region. As known in the art, the concave surface assists opening of the slit by inward flexing of the catheter wall when a low pressure condition exists in the lumen, thus facilitating aspiration. The second valve region 20 has a generally convex outer surface. As known in the art, the convex surface assists opening of the slit by outward flexing of the catheter wall when pressure is increased in the catheter lumen, which facilitates infusion.

Both valve regions include a protuberance in the region of the slit. In the first valve region, a protuberance 42 projects into the lumen. In the second valve region, a protuberance 44 projects radially outward into the environment. Slit 43 extends through protuberance 42 and slit 45 extends through protuberance 44.

During infusion, the inwardly projecting protuberance 42 enhances sealing of the first valve region (FIG. 7) when lumen pressure is increased creating an internal force 23' to open the second valve region. During aspiration, fluid is aspirated through the first valve region (FIG. 8), without interference from the protuberance 42, while sealing is enhanced at the second valve region by the force 21 acting on the outward projecting protuberance 44. The protuberance 42 on the infusion valve prevents inversion at the somewhat higher pressure differentials needed for operation of an aspiration valve with a convex outer surface.

In another embodiment, both valve regions have concave outer surfaces, with the first valve having an inwardly projecting protuberance and the second valve having an outwardly projecting protuberance. The first valve is used for aspiration and the second valve is used for infusion.

Figure 9:
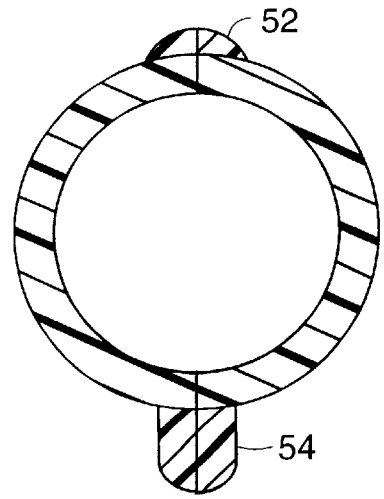
FIG. 9 is an end-on cross-section of another embodiment with a pair of valves as they would appear when viewed along the line 2—2 in FIG. 1, in a condition where neither infusion, nor aspiration is taking place.

Referring to FIG. 9, in another embodiment, both the first and second valve regions include outwardly projecting protuberances and the protuberances project different amounts. The first valve region protuberance 52, projects less than the second valve region protuberance 54. The valves are shown in a neutral pressure condition. For aspiration, a controlled lumen pressure causes the first valve region to invert while the larger protuberance 54 in the second valve region prevents inversion. For infusion, an increase in pressure causes both first and second valve regions to open.

Figure 10:
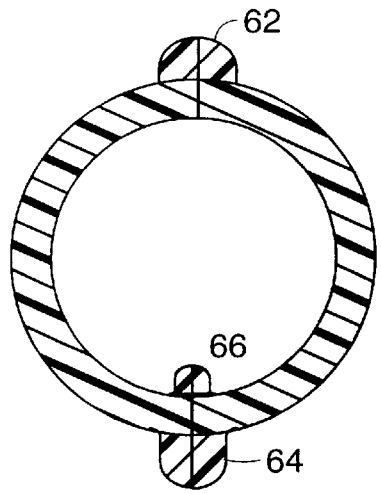
FIG. 10 is an end-on cross-section of another embodiment with a pair of valves as they would appear when viewed along the line 2—2 in FIG. 1, in a condition where neither infusion, nor aspiration is taking place.

Referring to FIG. 10, in another embodiment, the first valve region includes an outwardly projecting protuberance 62 while the second valve region includes both an outwardly projecting protuberance 64 and an inwardly projecting protuberance 66. The protuberance 66 projects to a lesser extent than the protuberance 64. The catheter is shown in a condition where neither infusion, nor aspiration is taking place. During infusion, the first valve opens first, at low initial pressure while inward projection 66 keeps the second valve sealed. At higher pressure, the sealing effect of-the inward projection 66 is overcome and infusion occurs through both of the values. Preferably, this embodiment is used for infusion only. In an alternate embodiment, both valves could be arranged for aspiration only, by forming both first and second regions with concave exterior surfaces.

Figure 11:
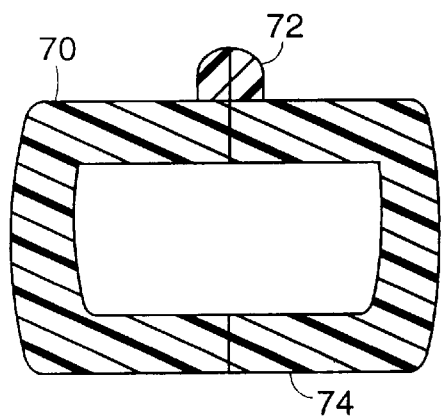
FIG. 11 is an end-on cross-section of another embodiment with a pair of valves as they would appear when viewed along the line 2—2 FIG. 1, in a condition where neither infusion, nor aspiration is taking place.

Referring to FIG. 11, another embodiment has a first valve region that includes a flat surface 70 with an outwardly projecting protuberance 72 and the second valve region also includes a flat region 74 without any protuberance. During aspiration, the protuberance 72 prevents opening of the first valve while aspiration occurs through the second valve. Infusion may occur through both the first and second valves.

Referring to FIGS. 12–13b, in another embodiment, a multilumen catheter is provided with multiple valve regions. Referring particularly to FIG. 12, the catheter 80 includes a catheter body 82 with an exterior surface 84 and an interior surface 86 between which the outer catheter wall thickness is defined. The interior surface, and an inner lumen wall 87, define a first lumen 88 and a second lumen 90. Both lumens 88, 90 are closed at the distal end 92 of the catheter and can be accessed through a luer coupling 94 at the proximal end of the catheter. The lumen 88 is in fluid communication with the environment through a first valve region 96 and a second valve region 100. The lumen 90 is in communication with the environment through a valve region 98.

Referring particularly to FIG. 13a, an end on cross section illustrates the valve regions 96, 98. Region 98 includes a generally convex outer wall surface geometry and an outwardly projecting protuberance 102, and a slit 97 extending through the wall and protuberance 102. The region 96 includes a generally concave outer wall surface geometry and an inwardly projecting protuberance 103 and a slit 99 extending through the wall and protuberance 103.

Referring to FIG. 13b, an end on cross section illustrates the valve region 100, which includes a generally convex catheter geometry and a slit 101 extending through the body. The region 96 also includes an outwardly projecting protuberance 104.

In operation, infusion can be carried out by increasing the pressure in the lumens 88 and 90, which causes the valves at regions 98, 100 to open and the valve at region 96 to seal tightly. For aspiration, pressure in lumen 88 is reduced which causes the valve at region 96 to open while the valve at region 100 seals tightly. Alternatively, or simultaneously, with infusion or aspiration as above, infusion can occur by increasing the pressure in lumen 88 to open the valve at region 100. Further multi-lumen catheter embodiments include catheters in which one or both of the lumens have a valve arrangement as described in FIGS. 1–11.

Figure 14:
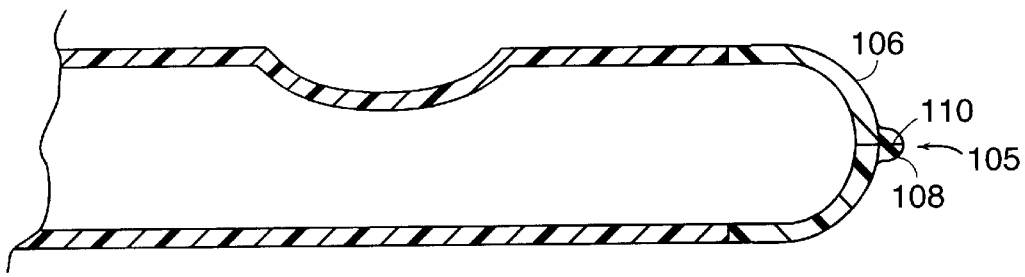
FIGS. 14 and 14a are longitudinal cross sections of another embodiment.
Figure 14A:
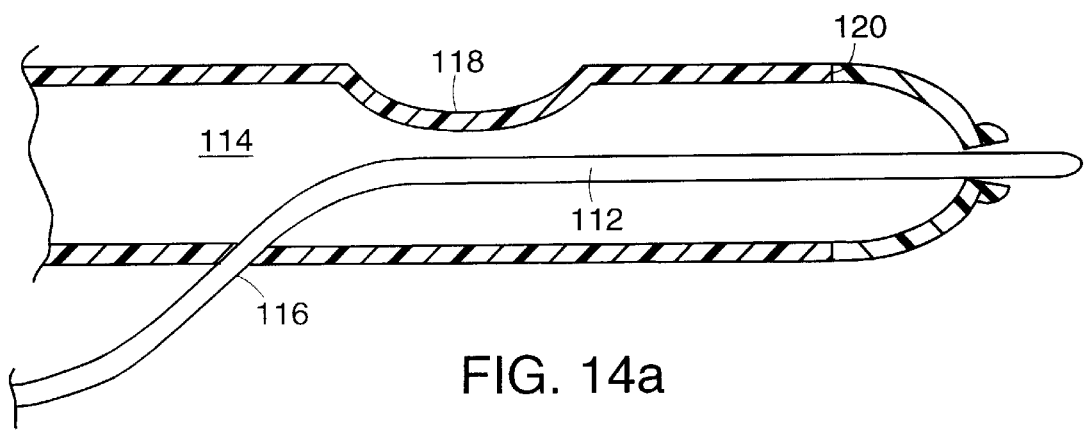

Referring to FIG. 14, in another embodiment, at least one slit valve 105 is provided at the forward-facing distal tip of the catheter. In this example, the tip has a generally convex, hemispherical outer surface 106 and a protuberance 108 extending outwardly from the catheter and including a slit 110 for use as an infusion valve. (Alternatively, the tip of the catheter may be concave for use as an aspiration valve.) Referring particularly to FIG. 14a, a catheter with a slit valve at the tip may make delivery over a guidewire 112 easier. The guidewire may extend through the valve 105 into the lumen 114. As illustrated, the guidewire may exit the lumen through a slit region 116 on the catheter wall to facilitate rapid exchange of the guidewire.- (Alternatively, the guidewire 112 may extend through the lumen to the proximal hub. The guidewire could also be passed through a valve on the side wall of the catheter, without passing through the valve at the tip.) The catheter may include additional valves, such as a slit valve 118 for infusion. The tip of the catheter may be manufactured as a separate component which is glued or molded, at attachment point 120, to the rest of the catheter body. In use, the catheter may be slid over the guidewire into a vessel. Infusion or aspiration may be conducted while the guidewire extends through the valve. Alternatively, the guidewire can be withdrawn from the valve prior to infusion or aspiration.

In additional embodiments, the catheter and valve types can be used in various combinations to create various combinations of infusion and aspiration effects using the principles illustrated above. A protuberance could be used on a catheter with a single slit valve. The protuberance may be trimmed manually by the physician prior to placement in the body to select the pressure differential needed to operate the valve. The protuberance could continue a distance along the catheter, for example, substantially the length of the catheter. The catheters can be sized for use in various parts of the body. A valve may have multiple intersecting slits. Multiple valves may be offset radially. In catheters with multiple valves, an infusion valve may be positioned proximal of an aspiration valve, for, e.g., flushing the downstream exterior of the catheter including the aspiration valve area with Urokinase to dissolve fibrin deposits. Alternatively, an infusion valve may be positioned distal of the aspiration valve, preferably near the distal end of the catheter, to facilitate flushing the full length of the lumen and avoiding dead volume. The catheters can be used in the vascular system for central venous access, to deliver, for example, drugs to a cancer patient. The catheter can be placed by a cutdown or the Seldinger technique.

Still further embodiments are within the following claims.

What is claimed is:

1. A catheter, comprising:
   (a) a first valve comprising a first protuberance and a first slit extending through said first protuberance and through said catheter, said first protuberance projecting from said catheter; and
   (b) a second valve comprising a second protuberance and a second slit extending through said second protuberance and through said catheter, said second protuberance projecting from said catheter,
said first protuberance's projection being greater than said second protuberance's projection.

2. The catheter of claim 1, wherein said first and second protuberances project from an exterior surface of the catheter.

3. A catheter including an exterior surface and at least one interior surface defining at least one lumen, said catheter comprising a valve comprising a first protuberance, a second protuberance, and a slit extending through said first and second protuberances and through said catheter, said first protuberance projecting from said exterior surface and said second protuberance projecting from the at least one interior surface into the at least one lumen.

4. The catheter of claim 3, wherein the projection of said first protuberance is greater than the projection of said second protuberance.

5. The catheter of claim 3, further comprising a second valve comprising a second slit extending through said catheter.

6. The catheter of claim 5, wherein said second valve further comprises a third protuberance through which the second slit extends.

7. A catheter including at least one interior surface defining at least one lumen, said catheter comprising a valve comprising a protuberance projecting from said catheter and a slit through said protuberance and said catheter, said valve opening inward into the at least one lumen in response to an aspiration threshold pressure differential, said valve opening outward in response to an infusion threshold pressure differential, said protuberance impacting the operation of said valve.

8. The catheter of claim 7 wherein said catheter comprises an exterior surface and said protuberance projects from the exterior surface, said protuberance impacting the operation of said valve by requiring said aspiration threshold pressure differential to be higher than said infusion threshold pressure differential before said valve will open into the at least one lumen.

9. The catheter of claim 7 wherein said protuberance projects into the at least one lumen, said protuberance impacting the operation of said valve by requiring said infusion threshold pressure differential to be higher than said aspiration threshold pressure differential before said valve will open outward.

10. The catheter of claim 7 further comprising a second valve comprising a second protuberance projecting from said catheter and a second slit through said second protuberance and said catheter, said second valve opening into the at least one lumen in response to a second aspiration threshold pressure differential, said second valve opening outward in response to a second infusion threshold pressure differential, said second protuberance impacting the operation of said second valve.

11. The catheter of claim 10 wherein said catheter comprises an exterior surface and said protuberance projects from the exterior surface, said protuberance impacting the operation of said valve by requiring said aspiration threshold pressure differential to be higher than said infusion threshold pressure differential before said valve will open into the at least one lumen, and wherein said second protuberance projects into the at least one lumen, said second protuberance impacting the operation of said second valve by requiring said second infusion threshold pressure differential relative to be higher than said second aspiration threshold pressure differential before said second valve will open outward.

12. The catheter of claim 10 wherein said protuberance projects from the exterior surface, said protuberance impacting the operation of said valve by requiring said aspiration threshold pressure differential relative to be higher than said infusion threshold pressure differential before said valve will open into the at least one lumen, and wherein said second protuberance projects from the exterior surface, said second protuberance impacting the operation of said second valve by requiring said second aspiration threshold pressure differential to be higher than said second infusion threshold pressure differential before said second valve will open into the at least one lumen, wherein said second aspiration threshold pressure differential is larger than said aspiration threshold pressure differential.

13. The catheter of claim 10 wherein said protuberance projects into the at least one lumen, said protuberance impacting the operation of said valve by requiring said infusion threshold pressure differential to be higher than said aspiration threshold pressure differential before said valve will open outward, and wherein said second protuberance projects from the at least one interior surface of the catheter body into the at least one lumen, said second protuberance impacting the operation of said second valve by requiring said second infusion threshold pressure differential to be higher than said second aspiration threshold pressure differential before said second valve will open outward, wherein said second aspiration threshold pressure differential is larger than said aspiration threshold pressure differential.

14. The catheter of claim 10 wherein said valve further comprises another protuberance through which said slit extends, said other protuberance impacting the operation of said valve by requiring one of said infusion threshold pressure differential or said aspiration threshold pressure differential to be higher than one of said second infusion threshold pressure differential or said second aspiration threshold pressure differential before said valve will open.

* * * * *